US008142760B2

(12) United States Patent
Winkelman

(10) Patent No.: US 8,142,760 B2
(45) Date of Patent: Mar. 27, 2012

(54) **VACCINATION FOR *LAWSONIA INTRACELLULARIS***

(76) Inventor: Nathan Len Winkelman, Sartell, MN (US)

( * ) Notice: Subject to any disclaimer, the term of this patent is extended or adjusted under 35 U.S.C. 154(b) by 62 days.

(21) Appl. No.: 12/205,017

(22) Filed: Sep. 5, 2008

(65) Prior Publication Data

US 2010/0062021 A1  Mar. 11, 2010

(51) Int. Cl.
| | |
|---|---|
| *A61K 49/00* | (2006.01) |
| *A61K 39/00* | (2006.01) |
| *A61K 39/38* | (2006.01) |
| *A61K 39/02* | (2006.01) |
| *A01N 63/00* | (2006.01) |
| *A01N 65/00* | (2009.01) |
| *C12N 1/12* | (2006.01) |
| *C12N 1/20* | (2006.01) |
| *C12N 1/00* | (2006.01) |

(52) U.S. Cl. ............ 424/9.2; 424/184.1; 424/234.1; 424/93.1; 424/93.4; 424/9.1; 435/252.1; 435/243

(58) Field of Classification Search ............ None
See application file for complete search history.

(56) References Cited

U.S. PATENT DOCUMENTS

| | | | |
|---|---|---|---|
| 5,885,823 | A | 3/1999 | Knittel et al. |
| 7,022,328 | B1 | 4/2006 | Panaccio et al. |
| 2003/0087421 | A1 | 5/2003 | Gebhart et al. |
| 2006/0024696 | A1 | 2/2006 | Kapur et al. |
| 2006/0286118 | A1 | 12/2006 | Vermeij |
| 2007/0014815 | A1* | 1/2007 | Kroll et al. ............ 424/234.1 |

FOREIGN PATENT DOCUMENTS

WO    WO 2006/099561 A1    9/2006

OTHER PUBLICATIONS

Gebhart et al 2003 American Association of Swine Veterinarians pp. 141-145.*
Winkelman et al 2003 American Association of Swine Veterinarians pp. 135-139.*
Walter et al 2001 Journal of Swine Health and Production vol. 9 No. 3 pp. 109-115.*
Boesen et al 2004 Veterinary Microbiology 103 (2004) pp. 35-45.*
Kinsley et al 2006 American Association of Swine Veterinarians pp. 157-161.*
"Aivlosin® 8.5 mg/g Oral Powder," product datasheet [online]. ECO Animal Health; London, UK. Copyright date unavailable [retrieved on May 15, 2009]. Retrieved from the Internet: <http://www.ecoanimalhealth.com/_assets/documents/45.pdf>; 3 pgs.
"Aivlosin® FG10," product datasheet [online]. ECO Animal Health; London, UK. Copyright date unavailable [retrieved on May 15, 2009]. Retrieved from the Internet: <http://www.ecoanimalhealth.com/_assets/documents/49.pdf>; 3 pgs.
"Aivlosin® FG50," product datasheet [online]. ECO Animal Health; London, UK. Copyright date unavailable [retrieved on May 15, 2009]. Retrieved from the Internet: <http://www.ecoanimalhealth.com/_assets/documents/50.pdf>; 3 pgs.
"Aivlosin® Soluble," product datasheet [online]. ECO Animal Health; London, UK. Copyright date unavailable [retrieved on May 15, 2009]. Retrieved from the Internet: <http://www.ecoanimalhealth.com/_assets/documents/46.pdf>; 3 pgs.
Armbruster et al., "Evaluation of Enteriosol® LI ileitis vaccine and Tylan® Premix efficacy against porcine proliferative enteropathy in a challenge model," *18th International Pig Veterinary Society Congress*; Hamburg, Germany: Jun. 27-Jul. 1, 2004: vol. 2, p. 579.
Bane et al., "Porcine proliferative enteropathy: a case-control study in swine herds in the United States," Jul. and Aug. 2001 *J. Swine Health Prod.* 9(4):155-158.
Bradford, "Clinical and economic effects of lincomycin in-feed (Lincomix®) and/or a porcine proliferative enterophathy (ileitis) vaccine (Enterisol® Ileitis) in pigs challenged with *Lawsonia intracellularis*," Jun. 2006 Pfizer Animal Health Technical Bulletin. Available online [retrieved on May 15, 2009] Retrieved from the Internet: <http://www.lincomix.com/pahimages/compliance_pdfs/LM_technical.pdf>; 8 pgs.
Carlson and Fangman, "Swine antibiotics and feed additives: food safety considerations," Jan. 2000 *Agricultural MU Guide* published by the University of Missouri—Columbia. Available online [retrieved on Apr. 24, 2009]. Retrieved from the Internet: <http://extension.missouri.edu/explorepdf/agguides/ansci/g02353.pdf>; 6 pgs.
Collins et al., "Studies on the ex vivo survival of *Lawsonia intracellularis*," Sep. and Oct. 2000 *J. Swine Health Prod.* 8(5):211-215.
Connor et al., "Inclusion of BMD® or BMD® plus 3 Nitro® in swine diets during ileitis vaccination," *Proceedings of the 35th American Association of Swine Veterinarians Annual Meeting*. San Diego, CA; Mar. 10, 2004: pp. 131-134.

(Continued)

*Primary Examiner* — Gary Nickol
*Assistant Examiner* — Nina Archie
(74) *Attorney, Agent, or Firm* — Mueting Raasch & Gebhardt, P.A.

(57) ABSTRACT

The present invention include a method of protecting an animal against *Lawsonia intracellularis* infections, the method including administering a dose of live virulent *L. intracellularis* to the animal, allowing a subclinical *L. intracellularis* infection to develop in the animal, and administering one or more antibiotics to the animal, wherein the one or more antibiotic is administered in a dose sufficient to abbreviate the subclinical *L. intracellularis* infection.

22 Claims, 1 Drawing Sheet

OTHER PUBLICATIONS

Connor et al., "Inclusion of BMD® or BMD® plus 3 Nitro® in swine diets during ileitis vacination," *18th International Pig Veterinary Society Congress*; Hamburg, Germany: Jun. 27-Jul. 1, 2004: vol. 1, p. 275.

Crane et al., "Efficacy of lincomycin in feed (Lincomix® Pfizer Animal Health) and/or porcine proliferative enteropathy (ileitis) vaccine (Enterisol® Ileitis; Boehringer Ingelheim) administered to pigs artificially challenged with *Lawsonia intracllularis*," *Proceedings of the 37th American Association of Swine Veterinarians Annual Meeting*. Kansas City, MO; Mar. 4-7, 2006: pp. 189-191.

"Denagard®/Tiamulin®," product information [online]. NOVARTIS Animal Health; Basel, Switzerland. Copyright 2007 [retrieved on Apr. 23, 2009]. Retrieved from the Internet: <http://www.denagard.com/product/en/index.shtml>; 2 pgs.

"Econor®," package insert [online]. NOVARTIS Animal Health; Basel, Switzerland. Copyright Mar. 2004 [retrieved on Apr. 23, 2009]. Retrieved from the Internet: <http://www.econor.com/product/en/index.shtml>; 21 pgs.

"Enterisol®," product datasheet [online]. Boehringer Ingelheim; St. Joseph, MO. Copyright date unavailable [retrieved on Apr. 23, 2009]. Retrieved from the Internet: <http://www.bi-vetmedica.com/product_sites/Enterisol_ileitis/reference.html#Product_Info>; 2 pgs.

"Enterisol® approved in Australia—first live swine vaccine ever in this market," Jun. 26, 2006 *Medical News Today*. Available online [retrieved on Apr. 24, 2009]. Retrieved from the Internet: <http://www.medicalnewstoday.com/printerfriendlynews.php?newsid=45926>; 2 pgs.

Gebhart et al., "Development of immunity to *Lawsonia intracellularis* in pigs fed Carbodox (Mecodox®)," *Proceedings of the 34th American Association of Swine Veterinarians Annual Meeting*. Orlando, FL; Mar. 8-11, 2003: pp. 141-145.

Gebhart et al., "Ileal symbiont *intracellularis*, an obligate intracellular bacterium of porcine intestines showing a relationship to *Desulfovibrio* species," Jul. 1993 *Int. J. Systemic Bacteriol.* 43(3):533-538.

Guedes et al., "Comparison of different methods for diagnosis of porcine proliferative enteropathy," *16h International Pig Veterinary Society Congress*; Melbourne, Australia: Sep. 17-20, 2000: vol. 2, p. 26.

Guedes et al., "Comparative study of an indirect immunofluorescent test and the immunoperoxidase monolayer assay for diagnosing porcine proliferative enteropathy," *16h International Pig Veterinary Society Congress*; Melbourne, Australia: Sep. 17-20, 2000: vol. 2, p. 61.

Guedes et al., "Comparison of different methods for diagnosis of porcine proliferative enteropathy," Apr. 2002 *Can. J. Vet. Res.* 66(2):99-107.

Guedes et al., "Serologic follow-up of a repopulated swine herd after an outbreak of proliferative hemorrhagic enteropathy," Oct. 2002 *Can. J. Vet. Res.* 66(4):258-263.

Guedes et al., "A comparative study of an indirect fluorescent antibody test and an immunoperoxidase monolayer assay for the diagnosis of porcine proliferative enteropathy," Sep. 2002 *J. Vet. Diagn. Invest.* 14(5):420-423.

Guedes et al., "Validation of an immunoperoxidase monolayer assay as a serologic test for porcine proliferative enteropathy," Nov. 2002 *J. Vet. Diagn. Invest.* 14(6):528-530.

Hammer, "The temporal relationship of fecal shedding of *Lawsonia intracellularis* and seroconversion in field cases," Jan. and Feb. 2004 *J. Swine Health Prod.* 12(1):29-33.

"Ileitis Technical Manual 3.0 ©," Table of contents [online]. Boehringer Ingelheim; St. Joseph, MO. Copyright 2006 [retrieved on Apr. 24, 2009]. Retrieved from the Internet: <http://www.thepigsite.com/publications/2/ileitis/>; 5 pgs.

"Ileitis: Characteristics and Costs of Ileitis," *Swine Health Management* [online]. Pfizer Animal Health; New York, NY. Copyright 2008 [retrieved on Apr. 24, 2009]. Retrieved from the Internet: <http://www.lincomix.com/Lincomix.aspx?country=US&species=SW&Drug=LX&sec=370>; 5 pgs.

Jones et al., "Enhanced detection of intracellular organism of swine proliferative enteritis, ileal symbiont *intracellularis*, in feces by polymerase chain reaction," Oct. 1993 *J. Clin. Microbiol.* 31(10):2611-2615.

Jordan et al., "Detection of *Lawsonia intracellularis* in swine using polymerase chain reaction methodology," Jan. 1999 *J. Vet. Diagn. Invest.* 11(1):45-49.

Just et al., "Monitoring of *Lawsonia intracellularis* by indirect serum immunofluorescence assay in a commercial swine production system," Mar. and Apr. 2001 *J. Swine Health Prod.* 9(2):57-61.

Kesl et al., "Tylan® Premix and Enterisol® LI ileitis vaccine evaluation in a *Lawsonia intracellularis* challenge model," *Proceedings of the 35th American Association of Swine Veterinarians Annual Meeting*. San Diego, CA; Mar. 10, 2004: pp. 139-142.

Kinsley et al., "Evaluation of the effectiveness of hyperimmunized chicken eggs for controlling *Lawsonia intracellularis* infection in growing swine," *Proceedings of the 35th American Association of Swine Veterinarians Annual Meeting*. San Diego, CA; Mar. 10, 2004: pp. 75-79.

Kinsley et al., "Elimination of *Lawsonia intracellularis* from pigs fed carbadox (Mecadox®)" *Proceedings of the 37th American Association of Swine Veterinarians Annual Meeting* Kansas City, MO; Mar. 4-7, 2006: pp. 157-161.

Kolb and Sick, "Summary of field trials implementing Enterisol® Ileitis against ileitis," *Proceedings of the 34th American Association of Swine Veterinarians Annual Meeting* Orlando, FL; Mar. 8-11, 2003: pp. 243-244.

Lawson et al., "Intracellular bacteria of porcine proliferative enteropathy: cultivation and maintenance in vitro," May 1993 *J. Clin. Microbiol.* 31(5):1136-1142.

"LINCOMIX® Feed Medication," product overview [online]. Pfizer Animal Health; New York, NY. Copyright 2008 [retrieved on Apr. 24, 2009]. Retrieved from the Internet: <http://www.lincomix.com/Lincomix.aspx?country=US&species=SW&drug=LM&sec=100>; 3 pgs.

"LINCOMIX® Injectable," product overview [online]. Pfizer Animal Health; New York, NY. Copyright 2008 [retrieved on Apr. 24, 2009]. Retrieved from the Internet: <http://www.lincomix.com/Lincomix.aspx?country=US&species=SW&drug=LJ&sec=110>; 2 pgs.

"LINCOMIX® Soluble Powder," product overview [online]. Pfizer Animal Health; New York, NY. Copyright 2008 [retrieved on Apr. 24, 2009]. Retrieved from the Internet: <http://www.lincomix.corn/Lincomix.aspx?country=US&species=SW&drug=LS&sec=120>; 2 pgs.

Marstellar et al., "Efficiency of Tylan® 200 injection for the treatment and control of porcine proliferative enteropathy caused by *Lawsonia intracellularis* in swine," *Proceedings of the 31st American Association of Swine Practitioners Annual Meeting*. Indianapolis, IN; Mar. 11-14, 2000: pp. 233-238.

Marstellar et al., "Monitoring the prevalence of *Lawsonia intracellularis* IgG antibodies using serial sampling in growing and breeding swine herds," May and Jun. 2003 *J Swine Health Prod.* 11(3):127-130.

McOrist et al., "Reproduction of porcine proliferative enteropathy with pure cultures of ileal symbiont *intracellularis*," Oct. 1993 *Infect. Immun.* 61(10):4286-4292.

McOrist et al., "Characerization of *Lawsonia intracellularis* gen. nov., sp. nov., the obligately *intracelluler* bacterium of porcine proliferative enteropathy," Oct. 1995 *Int. J. Systemic Bacteriol.* 45(4):820-825.

"Mecadox®," product datasheet [online]. Phibro Animal Health; Ridgefield Park, NJ. Copyright date unavailable [retrieved on Apr. 23, 2009]. Retrieved from the Internet: <http://www.phibroah.com/Phibro/Products/Catalog/Mecadox-Antimicrobial-For-Swine.html>; 1 pg.

Paradis et al., "Evaluation of Tylan® and Lincomix® administered in feed for the prevention of porcine proliferative enteropathy (ileitis)," *18th International Pig Veterinary Society Congress*; Hamburg, Germany: Jun. 27-Jul. 1, 2004: vol. 1, p. 303.

Paradis et al., "Evaluation of tylosin tartate in drinking water for treatment of porcine proliferative enteropathy (ileitis)," Jul. and Aug. 2004 *J. Swine Health Prod.* 12(4):176-181.

Paradis et al., "Subclinical ileitis produced by sequential dilutions of *Lawsonia intracellularis* in a mucosal homogenate challenge model," *Proceedings of the 36th American Association of Swine Veterinarians Annual Meeting* Toronto, Ontario CA; Mar. 5-8, 2005: pp. 189-191.
Roof, "Vaccinating for ileitis," *Proceedings of the Allen D. Leman Swine Conference* St. Paul, MN; Sep. 20-23, 2001: pp. 121-126.
Sims et al., "Efficacy of Aivlosin Premix for the control of (Porcine Proliferative Enteropathy (PPE; ileitis) in pigs experimentally infected with *Lawsonia intracellularis*," *19th International Pig Veterinary Society Congress* Copenhagen, Denmark; Jul. 16-19, 2006: vol. 2, p. 179.
Smith et al., "Gamma interferon influences intestinal epithelial hyperplasia caused by *Lawsonia intracellularis* infection in mice," Dec. 2000 *Infect. Immun.* 68(12):6737-6743.
Suh et al., "Detection of *Lawsonia intracellularis* in diagnostic specimens by one-step PCR," Jun. 2000 *J. Vet. Sci.* 1(1):33-37.
Tasker et al., "Use of Aivlosin in feed for control of ileitis in USA and Europe," *18th International Pig Veterinary Society Congress*; Hamburg, Germany: Jun. 27-Jul. 1, 2004: vol. 1, p. 256.
Tollis, "Standardization of tailorization of veterinary vaccines: a conscious endeavor against infectious disease of animals," 2006 *Ann Ist Super Sanita* 42(4):446-449.
"Tylan® 40," product datasheet [online]. ELANCO Animal Health—division of Eli Lilly; Indianapolis, IN. Copyright 2007 [retrieved on Apr. 23, 2009]. Retrieved from the Internet: <http://www.elanco.us/products/tylan_premix.htm>; 2 pgs.
"Tylan® 100," product datasheet [online]. ELANCO Animal Health—division of Eli Lilly; Indianapolis, IN. Copyright 2008 [retrieved on Apr. 23, 2009]. Retrieved from the Internet: <http://www.elanco.us/products/tylan_premix.htm>; 2 pgs.
Walter et al., "Serologic profiling and vaccination timing for *Lawsonia intracellularis*," Nov. and Dec. 2004 *J. Swine Health Prod.* 12(6):310-313.
Winkelman, "Management of ileitis on high health farms," *Proceedings of the Allen D. Leman Swine Conference* St. Paul, MN; 2000: pp. 73-76.
Winkelman et al., "Dose evaluation of Econor® (valnemulin hydrochloride) for the control of porcine proliferative enteritis using a *Lawsonia intracellularis* mucosal homogenate challenge," *16h International Pig Veterinary Society Congress*; Melbourne, Australia: Sep. 17-20, 2000: vol. 2, p. 33.
Winkelman et al., "Therapeutic impact of Econor® (valnemulin hydrochloride) on the development of porcine proliferative enteritis when supplied simultaneously to a *Lawsonia intracellularis* challenge," *16h International Pig Veterinary Society Congress*; Melbourne, Australia: Sep. 17-20, 2000: vol. 2, p. 70.
Winkelman et al., "An evaluation of BMD® and ChlorMax™ Chlortetracycline (CTC) for control of challenge-induced porcine proliferative enteropathy (PPE or ileitis) in swine," *Proceedings of the 32nd American Association of Swine Veterinarians Annual Meeting*. Nashville, TN; Feb. 24-27, 2001: pp. 77-82.
Winkelman et al., "Efficacy of Lincomix® soluble powder for the treatment and control of porcine proliferative enteropathy using a challenge model," *Proceedings of the 33rd American Association of Swine Veterinarians Annual Meeting*. Kansas City, MO; Mar. 2-5, 2002: pp. 199-201.
Winkelman et al., "Efficacy of BMD plus CTC for control of porcine proliferative enteropathy," *17th International Pig Veterinary Society Congress*; Ames, IA: Jun. 2-5, 2002: vol. 2, p. 190. Paper 365.
Winkelman et al., "Efficacy of Aivlosin for therapy of porcine proliferative enteropathy (PPE)," *17th International Pig Veterinary Society Congress*; Ames, IA: Jun. 2-5, 2002: vol. 2, p. 145. Paper 320.
Winkelman et al., "The impact of tiamulin administered in the water on the performance of growing swine with clinical porcine proliferative enteritis," *17th International Pig Veterinary Society Congress*; Ames, IA: Jun. 2-5, 2002: vol. 2, p. 197. Paper 372.
Winkelman et al., "Various doses of *L. intracellularis* in mucosal homogenate challenge model," *17th International Pig Veterinary Society Congress*; Ames, IA: Jun. 2-5, 2002: vol. 2, p. 211. Paper 386.
Winkelman et al., "Lincomycin-medicated feed for the control of porcine proliferative enteropathy (ileitis) in swine," May and Jun. 2002 *J. Swine Health Prod.* 10(3):106-110.
Winkelman et al., "An evaluation of BMD® plus Aureomycin® chlortetracycline (CTC), Tylan®, or Lincomix® for the control of challenge induced porcine proliferative enteropathy (PPE or ileitis) in swine," *Proceedings of the 34th American Association of Swine Veterinarians Annual Meeting*. Orlando, FL; Mar. 8-11, 2003: pp. 175-179.
Winkelman et al., "Correlation of clinical signs and diagnostic indicators of ileitis in pigs fed carbodox (Mecodox®)," *Proceedings of the 34th American Association of Swine Veterinarians Annual Meeting*. Orlando, FL; Mar. 8-11, 2003: pp. 135-139.
Winkelman et al., "Effectiveness of *Lawsonia intracellularis* specific chicken egg antibody to control ileitis in a swine disease challenge model," *18th International Pig Veterinary Society Congress*; Hamburg, Germany: Jun. 27-Jul. 1, 2004: vol. 1, p. 257.
Winkelman et al., "Determination of the dose rate of Aivlosin Soluble for the treatments of ileitis in *Lawsonia intracellularis* challenged pigs—a two study analysis," *19th International Pig Veterinary Society Congress*; Jul. 16-19, 2006: vol. 2, p. 171.
Winkelman, "Using a controlled exposure to *Lawsonia intracellularis* with carbodox (Mecadox ®) to stimulate immune response in pigs," *Proceedings of the American Association of Swine Veterinarians Annual Meeting* San Diego, CA; Mar. 8-11, 2008: pp. 223-225.
Winkelman, "Using a controlled exposure to *Lawsonia intracellularis* with carbodox (Mecadox ®) to stimulate immune response in pigs," Slides presented at the *American Association of Swine Veterinarians Annual Meeting* San Diego, CA; Mar. 8-11, 2008.
Collins et al., "The development of immunity to *Lawsonia intracellularis* in weaned pigs," in *Manipulating Pig Production VII*. Aitex International Pty Ltd.; Victoria, Australia: 1999. p. 241.
Guedes et al., "Onset and duration of fecal shedding, cell-mediated and humoral immune responses in pigs after challenge with a pathogenic isolate or attenuated vaccine strain of *Lawsonia intracellularis*," Feb. 2, 2003 *Vet. Microbiol.* 91(2-3):135-145.
Guedes et al,. "Relationship between the severity of porcine proliferative enteropathy and the infectious dose of *Lawsonia intracellularis*," Oct. 4, 2003 *Veterinary Record* 153:432-433.
Guedes and Gebhart, "Comparison of intestinal mucosa homogenate and pure culture of the homologous *Lawsonia intracellularis* isolate in reproducing proliferative enteropathy in swine," May 19, 2003 *Vet. Microbiol.* 93(2):159-166.
Kinsley et al., "Passive immunization of hamsters using hyper-immunized chicken eggs to control *Lawsonia intracellularis* infection: a model for growing swine," *Proceedings of the 34th American Association of Swine Veterinarians Annual Meeting*. Orlando, FL; Mar. 8-11, 2003: pp. 47-49.
Marsteller et al., "Efficacy of intramuscular tylosin for the treatment and control of porcine proliferative enteropathy caused by *Lawsonia intracellularis*," Winter 2001 *Veterinary Ther.* 2(1):51-60.
McOrist et al., "Polymerase chain reaction for diagnosis of porcine proliferative enteropathy," Aug. 1, 1994 *Vet. Microbiol.* 41(3):205-212.
McOrist and Gebhart, "Porcine proliferative enteropathies," in *Disease of Swine 8th Edition, Section 3—Bacterial Diseases* (Taylor et al., Eds). Iowa State University Press; Ames, IA. 1999. pp. 521-534.
Pelger et al., "Determining the efficacy of Tylan® intervention in a *Lawsonia intracellularis* challenge model designed to create subclinical ileitis," Poster abstract, *Allen D. Leman Swine Conference* St. Paul, MN; Sep. 17-20, 2005: p. 17.
Solano et al., "Impact of maternal immunity on subsequent challenge of piglets with *Heamophilus parasuis*," Meeting abstract. *14h International Pig Veterinary Society Congress*; Bologna, Italy; Jul. 7-10, 1996: p. 382.
Ward and Winkelman, "Recognizing the three forms of proliferative enteritis in swine," Feb. 1990 *Veterinary Medicine* 85:197-203.
Ward and Winkelman, "Diagnosing, treating, and controlling proliferative enteritis in swine," Mar. 1990 *Veterinary Medicine* 85:312-318.
Winkelman and Hawkins, "Evaluation of carbodox and neomycin-oxytetracycline for control of proliferative enteropathy (ileitis) in swine," Meeting abstract. *14h International Pig Veterinary Society Congress*; Bologna, Italy; Jul. 7-10, 1996: p. 278.
Winkelman, "Treatment and control of proliferative enteritis: research and empirical information," *Proceedings of the Allen D. Leman Swine Conference* St. Paul, MN; 1996: p. 60-62.

Winkelman, "Enteric clinical disease—'back to the basics'," *Proceedings of the 28th American Association of Swine Practitioners Annual Meeting*. Quebec City, CA; Mar. 1-4, 1997: pp. 353-359.

Winkelman et al., "An evaluation of aureomycin® chlortetracycline (CTC) granular feed additive for prevention or treatment of swine ileitis," *Proceedings of the 28th American Association of Swine Practitioners Annual Meeting*. Quebec City, CA; Mar. 1-4, 1997: pp. 79-81.

Winkelman, "Use of a challenge model to measure the impact of subclinical porcine proliferative enteritis on growth performance in pigs," *Proceedings of the 29th American Association of Swine Practitioners Annual Meeting*. Des Moines, IA; Mar. 7-10, 1998: pp. 209-211.

Winkelman, "Lincomycin feed medication and two water medications against ileitis caused by *Lawsonia intracellularis*," *Proceedings of the 29th American Association of Swine Practitioners Annual Meeting*. Des Moines, IA; Mar. 7-10, 1998: pp. 195-197.

Winkelman, "An evaluation of chlortetracycline feed additive for prevention or treatment of porcine proliferative enteropathy (PE or ileitis)," *Proceedings of the 15th International Pig Veterinary Society Congress*; Birmingham, UK; Jul. 5-9, 1998: p. 112.

Winkelman et al., "Dose determination of Lincomycin for treatment of porcine proliferative enteropathy," *Proceedings of the 15th International Pig Veterinary Society Congress*; Birmingham, UK; Jul. 5-9, 1998: p. 195.

Winkelman, et al., "Pilot evaluation of Lincomycin, Neomycin, and Lincomyacin + Spectinomycin for the treatment of proliferative ileitis in swine," *Proceedings of the 15th International Pig Veterinary Society Congress*; Birmingham, UK; Jul. 5-9, 1998: p. 194.

Winkelman, "Dose determination trial for Lincomycin in the control of porcine proliferative enteropathy;" *Proceedings of the Allen D. Leman Swine Conference* St. Paul, MN; Sep. 18-22, 1998: p. 27.

Winkelman, "Measurement of the correlation between lesion length and reduction in average daily gain using a *Lawsonia intracellularis* challenge model," *Proceedings of the 30th American Association of Swine Veterinarians Annual Meeting*. St. Louis, MO; Feb. 27-Mar. 2, 1999: pp. 241-242.

Winkelman, "Ileitis: an overview," in *Concepts in Pig Science 2nd Edition* (Lyons and Cole, Eds). Nottingham University Press: Thrumpton, Nottingham; UK: 2000. Title page, publishers page and p. 35-46.

Winkelman, "Ileitis: the disease. Porcine Proliferative Enteropathy," Slides presented with an oral presentation at the *Novartis National Sales Meeting*. Lake Tahoe, NV: Jan. 2008; 11 pgs.

Winkelman, "Clinical and subclinical ileitis—A summary of current knowledge," Slides presented with an oral presentation via *Novartis Canada Webinar*. Mar. 2008; 11 pgs.

Winkelman, "Ileitis and lincomycin's role to control and treat ileitis," Slides presented with an oral presentation at the *Pfizer National Sales Meeting*. San Diego, CA: Feb. 2008; 12 pgs.

* cited by examiner

|       | Day 0 inoculate | | | |
|-------|-----|-----|-----|-----|
| T1- Inoc. | Mecadox | Non-medicated | Mecadox | Non-medicated |

|       | Day 0 no inoculum | | | |
|-------|-----|-----|-----|-----|
| T2- CTL | Mecadox | Non-medicated | Mecadox | Non-medicated |

| Day -14+ | Day -3 ↱ Day 0 | Day 14 | Day 28 | Days 50 & 71 | Day 90 |
|----------|----------------|--------|--------|--------------|--------|
|          | IPMA           | Start MX | Stop MX | IPMA        | IPMA   |
|          | Fecals         | IPMA   | IPMA   | Fecals       | Fecals |
|          |                | Fecals | Fecals |              | Market |

VACCINATION FOR *LAWSONIA INTRACELLULARIS*

BACKGROUND

Porcine proliferative enteropathy (PPE, also known as ileitis) is an important enteric disease of swine, causing significant morbidity and mortality in swine herds throughout the world. The name "PPE" describes a group of diseases characterized by hyperplasia of crypt enterocytes in the ileum, jejunum, and large intestine. The causative agent is *Lawsonia intracellularis*, a Gram-negative obligate intracellular bacterium. The disease is widespread in pigs raised under various management systems and causes significant impact worldwide. See, for example, Barker et al., "The alimentary system," In: Jubb K V F, Kennedy P C, Palmer N, eds. Pathology of Domestic Animals. 4th ed. San Diego, Calif.: Academic Press; 1993:1-317; and McOrist and Gebhart, "Porcine proliferative enteropathies," In: Straw B E, D'Allaire S, Mengeling W L, Taylor D J, eds. Diseases of Swine. 8th ed. Ames, Iowa: Iowa State University Press; 1999:521-534.

The main clinical manifestations of PPE include the acute form, porcine hemorrhagic enteropathy (PHE), and the chronic form, porcine intestinal adenomatosis (PIA). Porcine hemorrhagic enteropathy usually occurs in pigs four to twelve months of age, particularly replacement breeding stock. Clinical signs include loose, watery stools with blood, gauntness, and high morbidity and mortality. Stressful events, such as mixing or sorting, shipping, and overcrowding, often precede an outbreak of PHE. Porcine intestinal adenomatosis commonly occurs in postweaned pigs six to twenty weeks of age. Failure to gain weight is the usual manifestation; other signs may include mild to moderate diarrhea, dullness, and apathy. See, for example, McOrist and Gebhart, "Porcine proliferative enteropathies," In: Straw B E, D'Allaire S, Mengeling W L, Taylor D J, eds. Diseases of Swine. 8th ed. Ames, Iowa: Iowa State University Press; 1999:521-5342.

The control of PPE is dependent in large part on the prudent administration of effective antimicrobial agents. And while an avirulent live vaccine, Enterisol®, is commercially available, there is a need for improved, economical methods for controlling *L. intracellularis* infections in pigs.

SUMMARY OF THE INVENTION

The present invention includes a method of vaccinating a pig against *Lawsonia intracellularis*, the method including administering a dose of live virulent *L. intracellularis* to the pig, allowing a subclinical *L. intracellularis* infection to develop in the pig, and administering one or more antibiotic to the pig, wherein the one or more antibiotic is administered in a dose sufficient to abbreviate the subclinical *L. intracellularis* infection.

In some embodiments of the method, the pig develops an immune response to *L. intracellularis*. In some embodiments, the immune response includes serum IgG antibodies to *L. intracellularis*. In some embodiments, the immune response includes cell-mediated immunity to *L. intracellularis*. In some embodiments, the immune response to *L. intracellularis* reduces the symptoms of further *L. intracellularis* infection in the pig.

In some embodiments of the method, the one or more antibiotic is administered to the pig more than 7 days, more than 10 days, more that 14 days, or more than 21 days after the administration of the dose of live virulent *L. intracellularis*.

In some embodiments of the method, the one or more antibiotic is administered to the pig at about 14 days after the administration of the dose of live virulent *L. intracellularis*.

In some embodiments of the method, the one or more antibiotic includes carbadox.

In some embodiments of the method, the dose of live virulent *L. intracellularis* is about $10^6$ or fewer *L. intracellularis* organisms per pig, about $10^5$ or fewer *L. intracellularis* organisms per pig, about 1 or fewer *L. intracellularis* organisms per pig, or about $10^4$ to about $10^6$ *L. intracellularis* organisms per pig.

In some embodiments of the method, the dose of live virulent *L. intracellularis* is obtained from an autogenous source.

In some embodiments of the method, the one or more antibiotic is administered to the pig in the feed.

In some embodiments of the method, the one or more antibiotic is administered to the pig in the drinking water.

In some embodiments of the method, the live virulent *L. intracellularis* is delivered orally to the pig in the drinking water or per os.

In some embodiments of the method, the dose of live virulent *L. intracellularis* is about $10^6$ or fewer *L. intracellularis* organisms per pig, about $10^5$ or fewer *L. intracellularis* organisms per pig, about $10^4$ or fewer *L. intracellularis* organisms per pig, or about $10^4$ to about $10^6$ *L. intracellularis* organisms per pig, the one or more antibiotic is administered to the pig more than 7 days after the administration of the dose of live virulent *L. intracellularis*, and the pig develops an immune response to *L. intracellularis*. In further embodiments, the one or more antibiotic includes carbadox.

In some embodiments of the method, the pig does not demonstrate a clinical manifestation of a *L. intracellularis* infection, wherein a clinical manifestation of a *L. intracellularis* infection is diarrhea, gauntness, depression, and combinations thereof.

The present invention includes a method of producing an immune response to *L. intracellularis* in an animal, the method including administering a dose of live virulent *L. intracellularis* to the animal, allowing a subclinical *L. intracellularis* infection to develop in the animal, and administering one or more antibiotic to the animal, wherein the one or more antibiotic is administered in a dose sufficient to abbreviate the subclinical *L. intracellularis* infection.

In some embodiments of the method, the immune response includes serum IgG antibodies to *L. intracellularis*.

In some embodiments of the method, the immune response includes cell-mediated immunity to *L. intracellularis*.

In some embodiments of the method, the immune response to *L. intracellularis* reduces the symptoms of further *L. intracellularis* infection in the pig.

In some embodiments of the method, the one or more antibiotic is administered to the pig more than 7 days, more than 10 days, more that 14 days, or more than 21 days after the administration of the dose of live virulent *L. intracellularis*.

In some embodiments of the method, the one or more antibiotic is administered to the pig at about 14 days after the administration of the dose of live virulent *L. intracellularis*.

In some embodiments of the method, the one or more antibiotic includes carbadox.

In some embodiments of the method, the dose of live virulent *L. intracellularis* is about $10^6$ or fewer *L. intracellularis* organisms per pig, about $10^5$ or fewer *L. intracellitlaris* organisms per pig, about $10^4$ or fewer *L. intracellularis* organisms per pig, or about $10^4$ to about $10^6$ *L. intracellularis* organisms per pig.

In some embodiments of the method, the dose of live virulent *L. intracellularis* is obtained from an autogenous source.

In some embodiments of the method, the one or more antibiotic is administered to the pig in the feed.

In some embodiments of the method, the one or more antibiotic is administered to the pig in the drinking water.

In some embodiments of the method, the live virulent *L. intracellularis* is delivered orally to the pig in the drinking water or per os.

In some embodiments of the method, the dose of live virulent *L. intracellularis* is about $10^6$ or fewer *L. intracellularis* organisms per pig, about $10^5$ or fewer *L. intracellularis* organisms per pig, about $10^4$ or fewer *L. intracellularis* organisms per pig, or about $10^4$ to about $10^6$ *L. intracellularis* organisms per pig and the one or more antibiotic is administered to the pig more than 7 days after the administration of the dose of live virulent *L. intracellularis*. In further embodiments, the one or more antibiotic includes carbadox.

In some embodiments of the method, the pig does not demonstrate a clinical manifestation of a *L. intracellularis* infection, wherein a clinical manifestation of a *L. intracellularis* infection is diarrhea, gauntness, depression, and combinations thereof.

The present invention includes a kit including a composition including live virulent *Lawsonia intracellularis* and instructions for the administration of the composition including live virulent *L. intracellularis* to a pig at a dose that results in the development of a subclinical *L. intracellularis* infection in the pig.

In some embodiments of the kit, the instructions provide for the administration of the composition including live virulent *L. intracellularis* at a dose wherein the pig does not demonstrate a clinical manifestation of a *L. intracellularis* infection, wherein a clinical manifestation of a *L. intracellularis* infection is diarrhea, gauntness, depression, and combinations thereof.

In some embodiments of the kit, the instructions for the administration of the composition including live virulent *L. intracellularis* include instructions for the administration at a dose of about $10^6$ or fewer live virulent *L. intracellularis* organisms per pig, about $10^5$ or fewer live virulent *L. intracellularis* organisms per pig, about $10^4$ or fewer live virulent *L. intracellularis* organisms per pig, or about $10^4$ to about $10^6$ live virulent *L. intracellularis* organisms per pig.

In some embodiments of the kit, the kit further includes instructions for the administration of one or more antibiotic to the pig, wherein the one or more antibiotic is administered in a dose sufficient to abbreviate the subclinical *L. intracellularis* infection. In some embodiments, the instructions provide for the administration of the one or more antibiotic at more than 7 days, at more than 10 days, at more that 14 days, or at more than 21 days after the administration of the live virulent *L. intracellularis*, and the one or more antibiotic is administered in a dose sufficient to abbreviate the subclinical *L. intracellularis* infection. In some embodiments, the one or more antibiotic includes carbadox.

In some embodiments of the kit, the dose of live virulent *L. intracellularis* is obtained from an autogenous source.

In some embodiments of the kit, the instructions provide for the administration of the one or more antibiotic to the pig in the feed.

In some embodiments of the kit, the instructions provide for the administration of the one or more antibiotic to the pig in the drinking water.

In some embodiments of the kit, the instructions provide for the administration of the live virulent *L. intracellularis* orally to the pig in the drinking water or per os.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

As used herein, an "effective dose" is that amount of a substance that provides a desired effect on the organism receiving the dose and may vary depending upon the purpose of administering the dose, the size and condition of the organism receiving the dose, and other variables recognized in the art as relevant to a determination of an effective dose. The process of determining an effective dose involves routine optimization procedures that are within the skill in the art.

BRIEF DESCRIPTION OF THE FIGURES

FIG. 1 shows the timeline for using a controlled exposure to *Lawsonia intracellularis* with MECADOX (carbadox) to stimulate immune responses in pigs.

DETAILED DESCRIPTION OF ILLUSTRATIVE EMBODIMENTS

The present invention includes methods of protecting an animal against infection by *Lawsonia intracellularis* or similar or otherwise related microorganisms. The method includes administering a dose of live virulent *L. intracellularis* microorganisms to the animal and administering one or more antibiotics to the animal, wherein the one or more antibiotics are administered in a dose sufficient to eliminate, abort, abbreviate, control, and/or treat, the *L. intracellularis* infection. In preferred embodiments, the dose of live virulent *L. intracellularis* microorganisms administered to the animal is a dose sufficient to lead to the development of a subclinical *L. intracellularis* infection in the animal.

*L. intracellularis* affects a wide range of animals, including, but not limited to, non-human primates, pigs, sheep, cattle, horses, donkeys, deer, goats, mice, rats, guinea pigs, rabbits, ferrets, foxes, kangaroos, and birds, such as, for example, ostriches, and emus. The methods of the present invention may be practiced in any of the animals affected by *L. intracellularis,* including, but not limited to, non-human primates, pigs, sheep, cattle, horses, donkeys, deer, goats, mice, rats, guinea pigs, rabbits, ferrets, foxes, kangaroos, and birds, such as, for example, ostriches, and emus. *L. intracellularis* is the causative agent of porcine proliferative enteropathy (PPE) in pigs (also referred to herein as "swine" or "hogs") and is a particularly great cause of losses in swine herds. In preferred embodiments, the methods of the present invention are practiced in pigs. And while preferred embodiments discuss the application of the methods disclosed herein to pigs, any methods, products, and uses discussed herein in reference to pigs may also be practiced with any of a range of animals, including, but not limited to, any of those discussed above.

The present invention includes a method of inducing an immune response to *L. intracellularis* in a pig. As used herein, the terms "Lawsonia intracellularis" and "*L. intracellularis*" mean the intracellular, curved gram-negative bacteria described in detail by Gebhart et al., 1993, *Int'l. J. of Systemic Bacteriology;* 43:533-538 and McOrist et al., 1995, *Int'l. J. of Systemic Bacteriology;* 45:820-825. The method includes administering a dose of live virulent *L. intracellularis* microorganisms to the pig. Once a subclinical infection has developed, one or more antibiotics are administered to the pig. The one or more antibiotics administered are effective to ameliorate, abort, eliminate, abbreviate, control, and/or treat the subclinical *L. intracellularis* infection. The one or more antibiotics are administered in a dose sufficient to ameliorate, abort, eliminate, control, and/or treat the subclinical *L. intracellularis* infection and an immune response to *L. intracellularis* is induced in the pig. Such an immune response may result in a substantial reduction of the symptoms of future *L. intracellularis* infection, such as PPE, in the pigs. Such an immune response may prevent a future *L. intracellularis* infection in a pig. Such an immune response may be a humoral immune response, a cellular immune response, and/or a mucosal immune response to *L. intracellularis*. A humoral immune response may include an IgG, IgM, IgA, IgD, and/or IgE response. The determination of a humoral, cellular, or mucosal immune response to *L. intracellularis* may be determined by any of a variety of methods, including, but not limited to, any of those described herein. For example, *L. intracellularis* antibodies can be detected by the immunoperoxidase monolayer assay (IPMA) or the indirect immunofluorescent assay (IFA). See, for example, Guedes et al., 2002, *Can J Vet Res;* 66(2):99-107; Guedes et al., 2002, *J Vet Diagn Invest;* 14:420-423; and Guedes et al., 2002, *J Vet Diagn Invest;* 14:528-530. Cellular immunity can be determined, for example, by a delayed type hypersensitivity (DTH) assay to intradermal injections of *L. intracellularis* or *L. intracellularis* antigen or by a serum test for antigen-specific serum gamma interferon (IFN-γ) production (see, for example, Guedes et al., 2003, *Vet Micro;* 9:135-145).

The induction of an immune response to *L. intracellularis* may include the priming and/or the stimulation of the immune system of the pig to respond to a future challenge with *L. intracellularis*. The induction of such an immune response may serve as a protective response, generally resulting in a reduction of the symptoms of *L. intracellularis* infection in pigs receiving a challenge with *L. intracellularis*. Preferably, the pig will display either a therapeutic or protective immunological response such that resistance to new infection will be enhanced and/or the clinical severity of the disease reduced. Such protection may be demonstrated by either a reduction or lack of the symptoms associated with *L. intracellularis* infection, including any of those described herein. In some embodiments, a method of the present invention may be used as a vaccination method, vaccinating an animal for the treatment and/or prophylaxis of infection in an animal by *L. intracellularis* or a related organism. Any of a wide variety of available assays may be used to determine the effectiveness of the vaccination method of the present invention. For example, clinical scores (including, but not limited to, fecal color, diarrhea, abdominal gut fill, and pig attitude), histopathology, lesion index, percent mortality, or average daily weight gain (adjusted for mortality) may be used. See, for example, Ileitis Technical Manual 3.0©, Boehringer Ingelheim Animal Health GmbH, 2006, available on the worldwide web at "thepigsite.com/publications/2/ileitis." Techniques for the detection of the presence of the *L. intracellularis* pathogen in histological sections of tissues or fecal samples may be used. Such techniques include, but are not limited to, immunohistochemistry (IHC) on histological slides of infected intestinal tissue, silver staining according to Warthin-Starry, immunofluorescence, electron microscopy and polymerase chain reaction (PCR). PCR may be performed using the sample preparation method, primers, and cycle parameters as described by, for example, Jones et al., 1993, *J Clin Microbiol;* 31:2611-2615; Jones et al., 1999, *J Vet Diagn Invest;* 11:45-49; McOrist et al., 1994, *Vet Microbiol;* 41(3):205-12; and Suh et al., 2000, *J Vet Sci;* 1(1):33-7.

Vaccines are typically grouped into two major classes, killed products and live products. Killed vaccine products provide bacterial or viral pathogens that have been inactivated and are incapable of replication in the host. Killed vaccines are no longer viable and are incapable of replication. With the present invention live, not killed, *L. intracellularis* organisms are administered to an animal. Such live *L. intracellularis* organisms are viable and capable of replication.

With live vaccine products, live bacterial or viral pathogens capable of replication in the host animal are administered. Such live vaccine products are modified in order to prevent the development of the disease when the vaccine is delivered to the animal. Such modified live bacterial or viral vaccines are avirulent. As used herein, the term "avirulent" represent modified pathogens not capable of causing disease in the host animal. At the present time, one attenuated, avirulent vaccine for *L. intracellularis* in swine is commercially available under the trade name Enterisol® Ileitis (Boehringer Ingelheim Vetmedica Inc., St. Joseph, Mo.). With the present invention, *L. intracellularis* organisms that are administered to an animal are virulent *L. intracellularis*. With the present invention, the *L. intracellularis* organisms that are administered have not been treated or selected to obtain an avirulent strain of *L. intracellularis*. With the present invention, avirulent *L. intracellularis* organisms are not administered. A variety of methods can be used to determine whether or not a particular *L. intracellularis* microorganism is virulent. For example, a susceptible vertebrate can be identified, infected with a sample containing the *L. intracellularis* microorganisms to be tested, and examined for the presence of a gross intestinal lesion.

With the present invention, a subclinical dose of *L. intracellularis* may be administered to an animal. A subclinical dose of *L. intracellularis* is a dose effective to result in a subclinical *L. intracellularis* infection in the animal. A subclinical infection is an infection with no overt clinical manifestations; a mild form of an infection in which few or no symptoms and signs are apparent or detectable by clinical examination or laboratory tests. As used herein, a subclinical *L. intracellularis* infection represents an infection in which the clinical manifestations of diarrhea, gauntness (abdominal appearance), and/or pig attitude (depression) are absent. With a subclinical *L. intracellularis* infection, one or more of the following may be present, the shedding of *L. intracellularis* organisms in the feces (detected, for example, by PCR), positive detection of *L. intracellularis* organisms in intestinal tissue at necropsy (for example, by IHC), histologically evident enterocyte hyperplasia (described in more detail, for example, by Paradis et al., Proc. 36$^{th}$ Annual Meeting of AASV, pp 189, 2005), seroconversion (as detected, for example, by the development of IgG antibodies for *L. intracellularis* by IPMA), and/or reduced pig performance (as measured, for example, by lessened weight gain).

A subclinical dose of *L. intracellularis* may be, for example, a dose per pig that does not result in one or more of diarrhea, gauntness (abdominal appearance), or pig attitude (depression). A subclinical dose of *L. intracellularis* may be a dose per pig that does not result in diarrhea, gauntness (abdominal appearance), and pig attitude (depression). A subclinical dose of *L. intracellularis* may be, for example, a dose per pig that does not result in diarrhea, gauntness (abdominal appearance), and/or pig attitude (depression), while one or more of the following may be observed, the shedding of *L. intracellularis* organisms in the feces, positive detection of *L. intracellularis* organisms in intestinal tissue at necropsy, histologically evident enterocyte hyperplasia, seroconversion and/or reduced pig performance.

In some embodiments, a subclinical dose of *L. intracellularis* is about $10^7$ or fewer *L. intracellularis* organisms per pig. In some embodiments, a subclinical dose of *L. intracellularis* is less than about $10^7$ *L. intracellularis* organisms per pig. In some embodiments, a subclinical dose of *L. intracellularis* is about $10^7$ *L. intracellularis* organisms per pig. In some embodiments, a subclinical dose of *L. intracellularis* is less than about $10^6$ *L. intracellularis* organisms per pig. In some embodiments, a subclinical dose of *L. intracellularis* is about $10^6$ *L. intracellularis* organisms per pig. In some embodiments, a subclinical dose of *L. intracellularis* is about 10 to about $10^6$ *L. intracellularis* organisms per pig. In some embodiments, a subclinical dose of *L. intracellularis* is about $10^5$ or fewer *L. intracellularis* organisms per pig. In some embodiments, a subclinical dose of *L. intracellularis* is less than about $10^5$ *L. intracellularis* organisms per pig. In some embodiments, a subclinical dose of *L. intracellularis* is about $10^5$ *L. intracellularis* organisms per pig. In some embodiments, a subclinical dose of *L. intracellularis* is about $10^4$ or fewer *L. intracellularis* organisms per pig. In some embodiments, a subclinical dose of *L. intracellularis* is less than about $10^4$ *L. intracellularis* organisms per pig. In some embodiments, a subclinical dose of *L. intracellularis* is about $10^4$ *L. intracellularis* organisms per pig. In some embodiments, a subclinical dose of *L. intracellularis* is about $10^3$ or fewer *L. intracellularis* organisms per pig. In some embodiments, a subclinical dose of *L. intracellularis* is less than about $10^3$ *L. intracellularis* organisms per pig. In some embodiments, a subclinical dose of *L. intracellularis* is about $10^3$ *L. intracellularis* organisms per pig. In some embodiments, a subclinical dose of *L. intracellularis* is about $10^4$ to about $10^6$ *L. intracellularis* organisms per pig. A dosage sufficient to result in a subclinical infection in animals other than pigs can be readily determined by one of skill in the veterinary arts, using the guidance provided herein.

When the method of the present invention is applied to a collection of animals, such as a herd or lot of animals, the dosage of *L. intracellularis* organisms that results in a subclincial infection may be a dose that results in a subclinical infection in a statistically significant portion of the animals, for example, about 75%, about 80%, about 85%, about 90%, about 95%, or about 99% of the animals. A statistically insignificant number of animals within the collection of animals may demonstrate one or more symptoms of a clinical infection, or demonstrate no infection at all.

*L. intracellitlaris* is an obligate intracellular bacterium which can not be cultured by normal bacteriological methods on conventional cell free media. Live, virulent *L. intracellularis* organisms for use in the methods of the present invention may be obtained in the form of an intestinal homogenate prepared from the intestinal tissue of one or more animals infected with *L. intracellularis*. For example, as described in more detail in Example 1, *L. intracellularis* may be prepared from mucosa harvested from the intestines of pigs having gross lesions consistent with PPE. To obtain the homogenate, mucosa is scraped from small intestines affected with moderate to severe PIA and (or) necrotic PPE lesions, and suspended at a 1:1 ratio in sucrose-phosphate-glutamate (SPG) buffer, pH 7.0, which contained sucrose (0.218 mol per L), monobasic potassium phosphate ($KH_2PO_4$; 0.0038 mol per L), dipotassium phosphate ($K_2HPO_4$; 0.0072 mol per L), and L-glutamic acid (0.0047 mol per L). The mucosal suspension is homogenized in a blender to obtain a uniform homogenized suspension. Homogenates may be stored at −70° C. until used, and thawed and stored on ice on days of use. Samples may be assayed for an enumeration of *L. intracellularis* (for example, by immunoperoxidase staining or by quantitative PCR) and to confirm the absence of enteric pathogens such as, for example, *Brachyspira* species, *Salmonella choleraesuis*, β-hemolytic *Escherichia coli*, porcine reproductive and respiratory syndrome (PRRS), and transmissible gastro-enteritis (TGE), ascarides, and coccidia. Homogenate may be diluted to proper concentration with SPG buffer. Homogenate may be aliquoted for convenient storage and administration. Mucosal homogenates may be stored by freezing, for example, at −70° C. The preparation of a homogenate may also be as described, for example, in Winkelman et al., 2002, *J Swine Health Prod;* 10(3):106-10; Pardis et al., 2004 *J Swine Health Prod;* 12(4):176-81; and Kinsley et al., pp. 157-161, AASV Proceedings 2006, Kansas City, Mo.; and U.S. Pat. No. 7,022,328.

The present invention includes the administration of live virulent *L. intracellularis* organisms that have been obtained from animals that have been either naturally or experimentally infected with *L. intracellularis*. In some aspects of the method of the present invention, the *L. intracellularis* that are administered may be a strain of virulent *L. intracellularis* that have been grown in a tissue culture system, including for example, any of those described in published U.S. Patent Application 2003/0087421; Lawson et al., 1993, *J Clin Microbiol;* 31(5): 1136-42; and McOrist et al., 1993, *Infect Immun;* 61(10): 4286-92.

In some embodiments of the present invention, *L. intracellularis* organisms may be obtained from an autogenous source. As used herein, the term "autogenous" means that the *L. intracellularis* organisms have been obtained from infected animals belonging to a restricted group or holding of animals and are administered to a similar group or holding of animals. For example, the autogenous pathogens may be obtained from animals of the same breed or genetic makeup, the same herd, same pig flow, same pig ownership, or the same geographic locale as the animals to be vaccinated. Such an autogenous vaccine (also referred to as autologous vaccine, autogenous/autologous vaccine, or A/A vaccine) presents advantages, allowing the preparation of a customized vaccine for treating a localized outbreak.

With the present invention, live virulent *L. intracellularis* are administered to an animal. "Administering" is given its ordinary and accustomed meaning of delivery by any suitable means recognized in the veterinary arts. Exemplary forms of administering include, but are not limited to, oral delivery, nasal delivery, anal delivery, direct puncture or injection, for example, by subcutaneous, intravenous, and intramuscular injection, and topical application. Oral delivery includes, for example, intragastric delivery by oral gavage and delivery in the drinking water or as a feed additive.

Administration may be in a single administration, or split for delivery as two, three, four, or more equal or unequal doses. Delivery of the separate doses may be, for example, about 4, about 6, about 8, about 10, about 12, about 24, about 36, about 48, or more hours may separate the administrations of the doses. For example, a dose may be administered to a pig in two equal divided doses administered about twenty-four hours apart.

Live virulent *L. intracellularis* may be for formulated for administration to animals by any of a wide variety of means known to the skilled person. Additional components, such as, for example, diluents, water, saline, dextrose, salts, stabilizing agents, preservatives, antibacterial agents, and antifungal agents may be added. See, for example Remington: The Science and Practice of Pharmacy, Twenty First Edition (2005).

With the present invention, live virulent *L. intracellularis* are administered to an animal at a subclinical dosage, which is then followed at an appropriate time interval by the administration of one or more antibiotics that abbreviate the subclinical infection. To abbreviate a subclinical *L. intracellularis* infection includes to treat, control or prevent the development of clinical signs of *L. intracellularis* infection, diarrhea, gauntness (abdominal appearance), and pig attitude (depression). To abbreviate a subclinical *L. intracellularis* infection may also include to reduce or decrease the evidence of a *L. intracellularis* infection in a pig's body or tissues, including, for example, to reduce or decrease the shedding of *L. intracellularis* organisms in the feces, and/or reduce or decrease the number of gross lesions in intestinal tissue at necropsy. To abbreviate a subclinical *L. intracellularis* infection may also include eliminating evidence of a *L. intracellularis* infection in a pig's body or tissues, including, for example to eliminate the shedding of *L. intracellularis* organisms in the feces, and/or eliminate gross lesions in intestinal tissue at necropsy.

An appropriate time interval is allowed to pass between the administration to the animal of the live virulent *L. intracellularis* and the administration of the one or more antibiotics. An appropriate time interval is a time interval adequate for the development in the animal of an immune response to *L. intracellularis* organisms and/or one or more *L. intracellularis* antigens. Such an immune response may be a humoral immune response, a cellular immune response, and/or a mucosal immune response. In some embodiments, an appropriate time interval is about 5 to about 21 days, about 5 to about 14 days, about 5 to about 10 days, about 5 to about 7 days, about 7 to about 21 days, about 7 to about 14 days, about 7 to about 10 days, or about 10 to about 21 days after the administration of the subclinical dose of *L. intracellularis*. In some embodiments, an appropriate time interval is 5 or more days, 7 or more days, 10 or more days, 14 or more days, or 21 or more days after the administration of the subclinical dose of *L. intracellularis*.

With the present invention, one or more antibiotics are administered to the animal, wherein the one or more antibiotics abbreviate and/or eliminate the subclinical *L. intracellularis* infection. The one or more antibiotics are administered for a period of time long enough to abbreviate and/or eliminate the subclinical infection. Any of a variety of available antibiotics may be administered to control, treat, and/or eliminate the subclinical *L. intracellularis* infection. As used herein an "antibiotic" is a chemotherapeutic agent, antibacterial agent, or antimicrobial agent that demonstrates activity (such as, for example, inhibiting the growth and/or killing) against microorganisms. An antibiotic of the present invention may be an antibiotic that demonstrates antimicrobial activity against *L. intracellularis*. An antibiotic of the present invention includes, but is not limited to, lincomycin (LINCOMIX®, Pfizer Animal Health) and other antibiotics of the lincosamines class, tylosin (Tylan®), tylvalosin tartarate (Aivlosin®), and other antibiotics of the macrolide class, chlortetracycline, carbadox (Mecadox®) and similar substituted quinoxaline antibiotics, arsanilic acid, tiamulin fumarate (Denagard® and Tiamutin®, Novartis Animal Health), valnemulin (Econor©), and other antibiotics of the pleuromutilin class, neomycin, oxytetracycline, roxarsone, and virginiamycin, and the combination of chlortetracycline and BMD.

An antibiotic of the present invention may be an antibiotic that is recognized as effective for the control or prevention of ileitis (PPE) in pigs. Recognition as effective for the control or prevention of ileitis in pigs includes, for example, approval by the FDA for such use. Such antibiotics include lincomycin (LINCOMIX®, Pfizer Animal Health), tylosin (TYLAN®, Elanco Animal Health), the combination of chlortetracycline (Aureomycin®, Alpharma Inc.) and BMD, and tiamulin (Denagard®, Novartis Animal Health).

In a preferred embodiment, the antibiotic is carbadox (also know by the tradename MECADOX, wherein the tradename MECADOX is also referred to herein as Mecadox®, Phibro Animal Health, Ridgefield Park, N.J.), and similar substituted quinoxaline antibiotics.

With the present invention, one or more antibiotics are administered to an animal. The one or more antibiotics may be formulated and administered to an animal by any of the wide variety of means known in the veterinary arts. Exemplary forms of administering include, but are not limited to, oral delivery, nasal delivery, anal delivery, direct puncture or injection, for example, by subcutaneous, intravenous, and intramuscular injection, and topical application. Oral delivery includes, but is not limited to, intragastric delivery by oral gavage and delivery in the drinking water or as a feed additive. Administration may be in a single administration, or split for delivery as two, three, four, or more equal or unequal doses. Delivery of the separate doses may be, for example, about 4, about 6, about 8, about 10, about 12, about 24, about 36, about 48, or more hours may separate the administrations of the doses. For example, a dose may be administered by to a pig in two equal divided doses administered about twenty-four hours apart. The one or more antibiotics may be formulated into medicaments by any of the variety of ways known in veterinary practice. The one or more antibiotics may be delivered at a dosage depending on the efficacies of the specific antibiotic used and such dosages are well known in the veterinary arts. For example, when delivered as a feed additive, Tylan® may be administered to pigs at a dose of 100 grams per ton (also referred to herein as gm/t) for twenty-one days followed by 40 gm/t of complete feed as the sole ration; lincomycin may be administered to pigs at a dose of 40 or 100 gm/t for twenty-one days; tiamulin may be administered to pigs at a dose of 35 gm/t for ten or more days; carbadox may be administered to pigs at a dose of 10 to 25 gm/t or 50 gm/t; and the combination of chlortetracycline and bacitracin may be delivered at the dose of 10 milligram (mg) chlortetracycline per pound of body and 30 gm/t BMD for up to 14 days.

In some embodiments of the present invention, live virulent *L. intracellularis* and one or more antibiotics are administered to a single animal. Normal swine husbandry practice is to keep many swine of similar ages and weights in a common holding area. In more preferred embodiments of the present invention, live virulent *L. intracellularis* and one or more antibiotics are administered en masse to an entire group of animals held in such a common holding area. For such mass administration, it may be particularly convenient to administer the live virulent *L. intracellularis* and/or the one or more antibiotics in the drinking water and/or as an additive in the animal feed.

In some embodiments of the present invention, the live virulent *L. intracellularis* and the one or more antibiotics are administered to an animal that has not been previously medicated with an antibiotic effective for the treatment and/or control of *L. intracellularis* infections. In some embodiments of the of the present invention, the live virulent *L. intracellularis* and the one or more antibiotics are administered to an animal that has been previously medicated with an antibiotic effective for the treatment and/or control of *L. intracellularis* infections, however, in this case, the premedication with an antibiotic should have been completed prior to the administration of the live virulent *L. intracellularis* to the animal, for example, completed at least about 1 day, at least about 2 days, at least about 3 days, at least about 5 days, at least about 7 days, at least about 10 days, at least about 14 days, or at least about 21 days before the administration of a subclinical dose of live virulent *L. intracellularis* to the animal.

With the method of the present invention, one or more additional immunologically active components effective in the treatment and/or prophylaxis of further disease causing organisms other than *L. intracellularis* may be administered to the animal, resulting in a multivalent immune response directed to both *L. intracellularis* and the one or more further disease causing organisms. For example, one or more of the vaccines, pathogens, immunological active components, or antigens discussed in WO 2006/099561 may be administered. In some embodiments, the one or more immunologically active components are effective to induce an immune response to *Salmonella* spp, *Escherichia coli*, or *Erysipelothrix rhusiopathiae*. The one or more immunologically active components may be administered prior to, co-incident to, and/or after the dose of live virulent *L. intracellularis*.

The invention also includes kits useful in practicing the methods of the present invention, including but not limited to, methods for controlling and/or preventing a *L. intracellularis* infection in an animal. Such kits include a composition of live virulent *L. intracellularis* and instructions for the dilution and/or administration of the composition of live virulent *L. intracellularis* to an animal at a dose effective to induce a subclinical *L. intracellularis* infection in the animal. A kit may further include instructions for the administration of the one or more antibiotics to the animal in a dose sufficient to treat, control, and/or eliminate the subclinical *L. intracellularis* infection.

A kit may further include one or more additional immunologically active components effective in the treatment and/or prophylaxis of further disease causing organisms, other than *L. intracellularis*, and may also include instructions for the administration of such additional immunologically active components.

A kit may include additional components, such as for example, one or more antibiotics, buffers and/or diluents.

In some embodiments, kits include a composition of live virulent *L. intracellularis* and instructions for the administration of the composition of live virulent *L. intracellularis* to a pig at a dose effective to induce a subclinical *L. intracellularis* infection in the pig. A kit may further include instructions for the administration of the one or more antibiotics to the pig in a dose sufficient to treat, control, and/or eliminate the subclinical *L. intracellularis* infection. In some embodiments, the instructions provide for the administration of the live virulent dose of *L. intracellularis* at various concentrations, for example, at a concentration of about $10^4$ to about $10^6$, about $10^6$ or fewer, about $10^5$ or fewer, and/or about $10^4$ or fewer *L. intracellularis* organisms per pig. In some embodiments, the kit further includes instructions for the sequential administration of *L. intracellularis* at a concentration of, for example, about $10^4$ to about $10^6$, about $10^6$ or fewer, about $10^5$ or fewer, and/or about $10^4$ or fewer live virulent *L. intracellularis* organisms per pig followed by the administration of the one or more antibiotics at, for example, at more that 7, at about 10 days, at about 14 days, or at about 21 days after the administration of the live virulent *L. intracellularis*.

In some embodiments, the instructions provide for the administration of the live virulent dose of *L. intracellularis* at a concentration of about $10^5$ *L. intracellularis* organisms per pig. In some embodiments, the kit further includes instructions for the sequential administration of *L. intracellularis* at a concentration of about $10^5$ live virulent *L. intracellularis* organisms per pig followed by the administration of the one or more antibiotics at, for example, more than 7 days, at about 10 days, at about 14 days, or at about 21 days after the administration of the live virulent *L. intracellularis*.

Each component of the kit may be enclosed within an individual container and various individual containers may be enclosed within a single package. Each component of the kit may be formulated for administration as described herein, and packaged appropriately for the intended route of administration.

The present invention is illustrated by the following examples. It is to be understood that the particular examples, materials, amounts, and procedures are to be interpreted broadly in accordance with the scope and spirit of the invention as set forth herein.

EXAMPLES

Example 1

Preparation of Challenge Inoculum

Challenge inoculum was prepared from mucosa harvested from the intestines of pigs having gross lesions consistent with PPE. To obtain the homogenate, mucosa was scraped from small intestines affected with moderate to severe PIA and (or) necrotic PPE lesions, and suspended at a 1:1 ratio in sucrose-phosphate-glutamate (SPG) buffer, pH 7.0, which contained sucrose (0.218 mol per L), monobasic potassium phosphate ($KH_2PO_4$; 0.0038 mol per L), dipotassium phosphate ($K_2HPO_4$; 0.0072 mol per L), and L-glutamic acid (0.0047 mol per L). The source for all reagents was Sigma (St Louis, Mo.). The mucosal suspension was homogenized in a blender to obtain an uniform homogenized suspension. Homogenates were stored at −70° C. until used, and thawed and stored on ice on days of use. Samples were submitted on ice to the Department of Veterinary Pathobiology, University of Minnesota, for enumeration of *L. intracellularis* by immunoperoxidase staining and quantitative PCR, and to confirm absence of the following enteric pathogens (methods in parentheses): *Brachyspira* species (dark field microscopy), *Salmonella choleraesuis* (culture on sheep blood agar, MacConkey agar, XLD agar, Brilliant Green agar), β-hemolytic *Escherichia coli* (culture on sheep blood agar, MacConkey agar). The mucosal homogenate was also screened for viruses, including porcine reproductive and respiratory syndrome (PRRS), and transmissible gastro-enteritis (TGE) (using known molecular diagnostics), and parasites, including ascarides and coccidia (by routine analysis). Homogenate was diluted to proper concentration with SPG buffer.

Example 2

Using a Controlled Exposure to *Lawsonia intracellularis* with Carbadox to Stimulate Immune Response in Pigs Proliferative enteropathy (also known as PE or ileitis) caused by *Lawsonia intracellularis* is a common infectious disease of swine worldwide. Field studies and experience have demonstrated immunological protection from *L. intracellularis* offers benefits to both growth performance and control of clinical and sub-clinical PE (Kolb and Sick, "Summary of field trials implementing Enterisol® Ileitis against ileitis," *Proc. American Association of Swine Veterinarians Annual Meeting*. Orlando, Fla. 2003:243-244). An immune response to *L. intracellularis* has been shown to develop in pigs following natural and experimental infections and after vaccination with avirulent live *L. intracellularis* organisms (Collins et al., "The Development of Immunity to Lawsonia intracellularis in weaned pigs," *Proc. of the 7th Biennial Conference of the Australasian Pig Science Assoc.*, Adelaide, Australia. 1999:241; and Roof, "Vaccinating for Ileitis," *Proc. Allen D. Leman Swine Conference*, St. Paul, Minn. 2001:121-126 2,3). Live *L. intracellularis* bacteria can be eliminated from pigs following experimental challenge by feeding carbadox, an antibacterial feed medication (Kinsley et al., "Elimination of *Lawsonia intracellularis* from pigs fed carbadox (Mecadox)," *Proc. American Association of Swine Veterinarians Annual Meeting*. Kansas City, Mo. 2006:157-161). This example demonstrates the development of protective immunity following controlled exposure to a field strain of virulent *L. intracellularis*. The clinical course of the exposure period was abbreviated with MECADOX (carbadox) 50 grams/ton.

Materials and Methods

Four groups of pigs totaling 1409 pigs, between 8 and 10 weeks of age and sourced from a single nursery site, were moved to a finishing barn containing four separate rooms. The barn was filled over four consecutive weeks, filling one room per week. Each group of approximately 350 pigs was weighed as a group before placement into a barn room. The four rooms were alternately assigned to two treatment groups, inoculated (T1) and non-inoculated (T2). Sixteen animals per room were randomly selected and individually identified with ear tags.

On day 0, T1 pigs received inoculum of mucosal homogenate from PE-diseased intestine. Samples of inoculum were submitted to a diagnostic lab for quantification of *L. intracellularis* organisms before administration. The inoculum was delivered to each pen through the watering system and calibrated to deliver an average dose of $10^{5\pm1.0}$ *L. intracellularis* organisms per pig over a 4-6 hour period. T2 pigs received no inoculum.

All pigs received MECADOX (carbadox) (50 g/ton) for at least 14 days in their nursery diets and up until day −3. Non-medicated feed was fed days −3 to 14 (exposure period) to both treatment groups. MECADOX (carbadox) 50 grams/ton medicated feed was fed to all pigs on days 14 to 28. From day 28 to end of study, all pigs received non-medicated feed. The overall experimental design is shown in FIG. 1.

Individual fecal and serum samples from tagged pigs were collected on days 0, 14, 28, 50, 71, and 90. Serum samples were submitted to a diagnostic lab and titered for IgG via the immunoperoxidase monolayer assay (IPMA) method. Fecal samples from days 14, 28, and 90 were submitted to a diagnostic lab and tested by PCR for *L. intracellularis*.

Close-out records were used to calculate ADG and feed conversion (F/G). All dead pigs were necropsied to determine cause of death and to evaluate for gross pathology typical of PE caused by *L. intracellularis*.

Means of pig weights and performance parameters (ADG, F/G) for both treatment groups were compared statistically using unpaired Student's t test. Laboratory diagnostic data (IPMA and PCR) and percent mortality, culls, and lights were tested using Fisher's exact test.

Results

Fecal PCR. Diagnostic laboratory analyses confirmed that a $10^{5\pm1.0}$ dose of mucosal homogenate inoculum was sufficient to establish patent infection with *L. intracellularis* in non-protected pigs. 94% (30/32) of sampled, non-medicated pigs receiving inoculum (T1) tested positive by fecal PCR for *L. intracellularis* 14 days post exposure. Conversely, 97% (31/32) of non-exposed, non-medicated pigs (T2) were negative by fecal PCR for *L. intracellularis* on day 14. On day 28, after receiving 14 days of MECADOX (carbadox) therapy, 100% of sampled, infected pigs that received inoculum (T1) were negative by fecal PCR for *L. intracellularis* organisms. At the end of the study, 16% (5/31) of these same T1 pigs tested positive by fecal PCR but exhibited no clinical signs of PE. All non-exposed pigs remained PCR negative until the end of study. These results are shown in Table 1.

TABLE 1

Number of fecal PCR positive pigs/pigs sampled

| | Day of Study | | |
|---|---|---|---|
| | 14 | 28 | 90 |
| T1 - Inoculated | 30/32$^a$ | 0/32 | 5/31$^a$ |
| T2 - Non-Inoculated | 1/32$^b$ | 0/32 | 0/32$^b$ |

Within each column, treatment values with unlike superscripts differ at P < 0.05

Serology. Diagnostic laboratory testing confirmed that by day 90 post exposure, 94% (30/32) of the sampled, inoculated pigs had developed IgG antibodies for *L. intracellularis* tested by IPMA. Conversely 91% (29/32) of the sampled, non-inoculated pigs remained negative for antibodies to *L. intracellularis*. These results are shown in Table 2.

TABLE 2

Cumulative number of IPMA positive pigs/pigs sampled

| | Day of Study | | | | | |
|---|---|---|---|---|---|---|
| | 0 | 14 | 28 | 50 | 71 | 90 |
| T1 - Inoculated | 0/32 | 0/32$^a$ | 18/32$^a$ | 20/32$^a$ | 23/32$^a$ | 30/32$^a$ |
| T2 - Non-inoculated | 0/32 | 1/32$^{a*}$ | 0/32$^b$ | 0/32$^b$ | 0/32$^b$ | 3/32$^{b*}$ |

*IPMA reported as weak positive Within each column, treatment values with unlike superscripts differ at P < 0.05

Performance. While differences in growth performance were not statistically significant (p>0.05), inoculated pigs (T1) gained numerically faster than non-inoculated pigs (1.945 vs. 1.880 ADG respectively) and converted feed slightly more efficiently (2.840 vs. 2.895 F/G). These results are shown in Table 3.

TABLE 3

Performance summary

| | No. head in | Avg. wt. in | No. head mktd. | Avg. mkt. wt. | ADG | F/G |
|---|---|---|---|---|---|---|
| T1 - Inoculated | 692 | 58.01$^a$ | 676 | 274.25$^a$ | 1.945$^a$ | 2.840$^a$ |
| T2 - Non-Inoculated | 717 | 57.54$^a$ | 691 | 270.83$^a$ | 1.880$^a$ | 2.895$^a$ |

Within each column, treatment values with unlike superscripts differ at P < 0.05

Attrition. Attrition due to mortality was higher (3.49% vs. 2.02%), but not statistically different, for the non-inoculated pigs (T2). PE caused by L. intracellularis infection contributed to no deaths in either group during the course of the study. These results are shown in Table 4.

TABLE 4

Attrition: percent and number mortality, culls, and lights*

| | % mort. (no.) | % culls (no.) | % lights (no.) | Causes of mortality |
|---|---|---|---|---|
| T1 - Inoculated | 2.02$^a$ (14) | .29$^a$ (2) | 1.48$^a$ (10) | 3 HBS, 3 lame, 3 umbilical hernia, 1 rectal stricture, 1 tail bite, 3 unknown |
| T2 - Non-inoculated | 3.49$^a$ (25) | .14$^a$ (1) | 1.01$^a$ (7) | 6 HBS, 3 lame, 1 umbilical hernia, 3 ulcer, 1 rectal stricture, 1 downer, 10 unknown |

*Lights = pigs ≦ 200 lb. live mkt. wt. or ≦163 lb. carcass wt.
Within each column, treatment values with unlike superscripts differ at $P < 0.05$ Discussion Pigs inoculated with mucosal homogenate containing a field strain of virulent L. intracellularis developed patent infections evidenced by the shedding of L. intracellularis organisms in their feces. This infection generated an immunological response as measured by IPMA testing of serum for antibodies. It was not determined if this immunity was protective as no subsequent natural L. intracellularis challenge occurred. The research barn used for this study had a history of endemic, clinical ileitis in pigs. The previous group of pigs experienced an acute proliferative hemorrhagic enteropathy (PHE) outbreak in late finishing diagnosed by both, postmortem examination and positive fecal PCR analysis. However, no clinical signs or mortality caused by L. intracellularis infection was observed in any pigs during this study.

MECADOX (carbadox) medication clearly abbreviated the L. intracellularis infection when administered 14 days post inoculation. 100% of the pigs previously shedding bacteria were negative by fecal PCR for L. intracellularis after receiving Mecadox® therapy for 14 days.

A controlled exposure to autogenous, live L. intracellularis inoculum offers veterinarians another program for immunizing pigs against ileitis. Feeding carbadox, a bactericidal compound capable of eliminating the immunizing inoculum and ensuing infection of live L. intracellularis organisms is critical to the success of a controlled exposure program.

Example 3

Lawsonia intracellularis (Ileitis) Challenge Experiment

This example will compare the clinical, pathological, laboratory, and performance parameters in "controlled immunity" pigs vaccinated with ileitis autogenous vaccine followed by either MECADOX (carbadox) 25 g/ton (also referred to herein as "Mec 25") or MECADOX (carbadox) 50 g/ton (also referred to herein as "Mec 50") or pigs vaccinated with Enterisol Ileitis® all followed by a heavy Lawsonia intracellularis (Li) disease challenge four weeks after vaccination.

All pigs in T1, T2, T3, and T4 will be humanely euthanized on Day 52, 24 days after the Li oral gavage. Clinical parameters to be measured are Fecal Scores (0-3), Abdominal Appearance Score (0-2), and Pig Demeanor Score (0-2). Ileitis pathology to be measured includes gross PPE lesion scores, lesion length and IHC scores (0-4). Laboratory analysis on serum IPMA, and fecal PCR will be completed at specific time points throughout the study. Performance parameters of ADG, FCR, and ADFI will be recording a various study time intervals. Unless otherwise specified, procedures are the same as those described in Example 2. The trial design is outlined in Table 5.

TABLE 5

Trial Design

| Treatment | Treatment Description | Days of Medication | Animals per Treatment | Replicate per Treatment | Pigs/Pen |
|---|---|---|---|---|---|
| T1 - Neg Ctl | No Vaccine<br>D28 - Li challenge<br>D52 - Euthanize all | N/A | 36 | 6 | 6 |
| T2 - Enterisol Ileitis® | D0 - Bi Vaccine<br>D28 - Li challenge<br>D52 - Euthanize all | N/A | 36 | 6 | 6 |
| T3 - Autogenous Ileitis w/ Mec 25 | D0 - Autogenous Vaccine<br>D14-D28 Mec 25<br>D28 - Euthanize 12 pigs<br>D28 - Li challenge<br>D52 - Euthanize all | D14-D28 Mecadox 25 | 48 | 8 | 6 |
| T4 - Autogenous Ileitis w/Mec 50 | D0 - Autogenous Vaccine<br>D14-D28 Mec 50<br>D28 - Euthanize 12 pigs<br>D28 - Li challenge<br>D52 - Euthanize all | D14-D28 Mecadox 50 | 48 | 8 | 6 |

TABLE 5-continued

Trial Design

| Treatment | Treatment Description | Days of Medication | Animals per Treatment | Replicate per Treatment | Pigs/Pen |
|---|---|---|---|---|---|
| T5 - Positive Control | D0 - Autogenous Vaccine D28 - Euthanize all 12 pigs | N/A | 12 | 2 | 6 |
| TOTAL | | | 180 pigs | 30 Pens | |

In the T1 negative control group, all animals will be challenged with a heavy dose of $10^9$ L. intracellularis at Day 28, and euthanized at Day 52. A dose of $10^9$ L. intracellularis has been previously shown to induce a clinical infection.

In the Enterisol Ileitis® vaccinated group (T2), animals will be vaccinated with Enterisol Ileitis® on Day 0 (following manufacturer's directions), challenged with a heavy dose of $10^9$ L. intracellularis at Day 28, and euthanized at Day 52.

In the T3 autogenous vaccine with Mec 25 group, an autogenous vaccine of $10^5$ L. intracellularis will be administered to the animals on Day 0, followed by the administration of MECADOX (carbadox) antibiotic at 25 gm/ton at Day 14 to Day 28 for a 14 day medication period. This will be following methods described in more detail in Example 2. On Day 28, 12 animals will be euthanized and the remaining animals will be challenged with a heavy dose of $10^9$ L. intracellularis at Day 28, and euthanized at Day 52.

In the T4 autogenous vaccine with Mec 50 group, an autogenous vaccine of $10^5$ L. intracellularis will be administered to the animals on Day 0, followed by the administration of MECADOX (carbadox) antibiotic at 50 gm/ton at Day 14 to Day 28 for a 14 day medication period. This will be according to methods described in more detail in Example 2. On Day 28, 12 animals will be euthanized and the remaining animals will be challenged with a heavy dose of $10^9$ L. intracellularis at Day 28, and euthanized at Day 52.

In the T5 positive control group, an autogenous vaccine of $10^5$ L. intracellularis will be administered to the animals on Day 0, no MECADOX (carbadox) antibiotic will be administered, and all animals will be euthanized on Day 28. These 12 pigs are used as vaccinated controls to compare the T3 and T4 pigs euthanized on Day 28.

Example 4

Exposure of Vaccinated Animals to L. intracellularis

Animals vaccinated according the method described in more detail in Example 2, with a subclinical dose of virulent L. intracellularis followed by the administration of an antibiotic effective to treat the L. intracellularis infection, will be purposely exposed to a subsequent natural L. intracellularis challenge at least four weeks after vaccination. Animals will be monitored all the way to market. Inoculated and non-inoculated animals will be monitored for clinical signs of L. intracellularis infection, such as diarrhea, gauntness, depression, and fecal shedding, and for economic efficacies, such as differences in growth performance and attrition due to mortality, light weight and cull pigs. Inoculated animals will be compared to non-vaccinated animals.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of producing an immune response to Lawsonia intracellularis in a pig, the method comprising:
    administering a subclinical dose of live virulent Lawsonia intracellularis to the pig;
    wherein the dose of live virulent Lawsonia intracellularis is $10^4$ to $10^6$ Lawsonia intracellularis organisms per pig;
    allowing a subclinical Lawsonia intracellularis infection to develop in the pig;
    wherein a subclinical infection is an infection in which diarrhea, gauntness, and depression are absent; and
    administering one or more antibiotic to the pig, wherein the one or more antibiotic is administered in a dose sufficient to abbreviate the subclinical Lawsonia intracellularis infection.

2. The method of claim 1, wherein the pig develops an immune response comprising serum IgG antibodies to Lawsonia intracellularis.

3. The method of claim 1, wherein the pig develops an immune response comprising cell-mediated immunity to Lawsonia intracellularis.

4. The method of claim 1, wherein the one or more antibiotic comprises carbadox.

5. The method of claim 1, wherein the one or more antibiotic is administered to the pig in the feed.

6. The method of claim 1, wherein the one or more antibiotic is administered to the pig in the drinking water.

7. The method of claim 1, wherein the live virulent Lawsonia intracellularis is delivered orally to the pig in the drinking water or per os.

8. The method of claim 1, wherein the one or more antibiotic is administered to the pig beginning at 10 or more days after the administration of the dose of live virulent Lawsonia

*intracellularis* or beginning at 14 or more days after the administration of the dose of live virulent *Lawsonia intracellularis*.

9. The method of claim 1, wherein the one or more antibiotic is administered to the pig beginning more than 7 days after the administration of the dose of live virulent *Lawsonia intracellularis*.

10. The method of claim 1, wherein the dose of live virulent *Lawsonia intracellularis* is obtained from an autogenous source.

11. The method of claim 1 wherein the subclinical dose of live virulent *Lawsonia intracellularis* comprises an intestinal homogenate.

12. The method of claim 1, wherein a time interval of more than 7 days but no more that 21 days is allowed to pass between administration of the dose of live virulent *Lawsonia intracellularis* and initiation of administration of the one or more antibiotic.

13. The method of claim 1, wherein the immune response reduces the symptoms of future *Lawsonia intracellularis* infections in the pig.

14. A method of producing an immune response to Lawsonia intracellularis in a pig, the method comprising:
   administering a subclinical dose of live virulent *Lawsonia intracellularis* to the pig;
   wherein the dose of live virulent *Lawsonia intracellularis* is $10^4$ to $10^6$ *Lawsonia intracellularis* organisms per pig;
   allowing a subclinical *Lawsonia intracellularis* infection to develop in the pig;
   wherein a subclinical infection is an infection in which diarrhea, gauntness, and depression are absent; and
   administering one or more antibiotic to the pig, wherein the one or more antibiotic is administered in a dose sufficient to abbreviate the subclinical *Lawsonia intracellularis* infection;
   wherein the one or more antibiotic is administered to the pig beginning more than 7 days after the administration of the dose of live virulent *Lawsonia intracellularis*.

15. The method of claim 14, wherein the pig develops an immune response comprising serum IgG antibodies to *Lawsonia intracellularis* and/or cell-mediated immunity to *Lawsonia intracellularis*.

16. The method of claim 14, wherein the one or more antibiotic comprises carbadox.

17. The method of claim 14, wherein the one or more antibiotic is administered to the pig beginning at 10 or more days after the administration of the dose of live virulent *Lawsonia intracellularis* or beginning at 14 or more days after the administration of the dose of live virulent *Lawsonia intracellularis*.

18. The method of claim 14, wherein a time interval of more than 7 days but no more that 21 days is allowed to pass between administration of the dose of live virulent *Lawsonia intracellularis* and initiation of administration of the one or more antibiotic.

19. The method of claim 14 wherein the immune response reduces the symptoms of future *Lawsonia intracellularis* infections in the pig.

20. A method of producing an immune response to *Lawsonia intracellularis* in a pig, the method comprising:
   administering a subclinical dose of live virulent *Lawsonia intracellularis* to the pig;
   wherein the dose of live virulent *Lawsonia intracellularis* is $10^4$ to $10^6$ *Lawsonia intracellularis* organisms per pig;
   allowing a subclinical *Lawsonia intracellularis* infection to develop in the pig;
   wherein a subclinical infection is an infection in which diarrhea, gauntness, and depression are absent; and
   administering one or more antibiotic to the pig, wherein the one or more antibiotic is administered in a dose sufficient to abbreviate the subclinical *Lawsonia intracellularis* infection;
   wherein a time interval of more than 7 days but no more that 21 days is allowed to pass between administration of the dose of live virulent *Lawsonia intracellularis* and initiation of administration of the one or more antibiotic.

21. The method of claim 20, wherein the one or more antibiotic comprises carbadox.

22. The method of claim 20, wherein the dose of live virulent *Lawsonia intracellularis* is obtained from an autogenous source.

* * * * *